US 9,439,812 B2
Sep. 13, 2016

(12) United States Patent
Komatsubara (54) ABSORBENT ARTICLE FOR PET ANIMALS

(71) Applicant: UNICHARM CORPORATION, Shikokuchuo-shi, Ehime (JP)

(72) Inventor: Daisuke Komatsubara, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 25 days.

(21) Appl. No.: 14/401,410

(22) PCT Filed: Jun. 16, 2014

(86) PCT No.: PCT/JP2014/065950
§ 371 (c)(1),
(2) Date: Nov. 14, 2014

(87) PCT Pub. No.: WO2015/005068
PCT Pub. Date: Jan. 15, 2015

(65) Prior Publication Data
US 2016/0008183 A1    Jan. 14, 2016

(30) Foreign Application Priority Data
Jun. 6, 2014 (JP) .................... 2014-118171

(51) Int. Cl.
*A61F 13/49* (2006.01)
*A01K 23/00* (2006.01)
*A61F 13/15* (2006.01)

(52) U.S. Cl.
CPC ......... *A61F 13/49014* (2013.01); *A01K 23/00* (2013.01); *A61F 2013/15186* (2013.01)

(58) Field of Classification Search
CPC ............ A01K 23/00; A61F 13/49009; A61F 13/49011; A61F 13/49014; A61F 13/4752; A61F 13/4753
See application file for complete search history.

(56) References Cited

U.S. PATENT DOCUMENTS

| 5,005,525 A * | 4/1991 | Stanton ................. A01K 23/00 |
| | | 119/838 |
| 5,947,949 A * | 9/1999 | Inoue .................. A61F 13/4942 |
| | | 604/385.08 |
| 6,368,313 B1 * | 4/2002 | Howard ................. A01K 23/00 |
| | | 119/850 |

(Continued)

FOREIGN PATENT DOCUMENTS

| DE | 3132671 A1 * | 4/1982 | ............. A01K 23/00 |
| IT | EP 0958741 A2 * | 11/1999 | ............. A01K 23/00 |

(Continued)

OTHER PUBLICATIONS

International Search Report mailed Jul. 15, 2014 in International Application No. PCT/JP2014/065950.

*Primary Examiner* — Lynne Anderson
*Assistant Examiner* — Kathryn E Ditmer
(74) *Attorney, Agent, or Firm* — Hauptman Ham, LLP (57) ABSTRACT

The present invention aims to provide an absorbent article for pet animal ensuring a high fit of the absorbent core along the end edges thereof to the body of pet animal.
An absorbent article further includes ventral side elastic element extending in the transverse direction (X) in the ventral region, the absorbent core is located in an area extending from an opening provided in the intermediate region for insertion of tail of pet animal toward the side of the ventral region and the absorbent core has a first end portion located on the side of the ventral region, and the first end portion of the absorbent core overlaps the ventral side elastic element in a planar view.

8 Claims, 11 Drawing Sheets

(56) References Cited

U.S. PATENT DOCUMENTS

| | | |
|---|---|---|
| 2006/0217678 A1 | 9/2006 | Ikegami et al. |
| 2010/0229803 A1 | 9/2010 | Meissner et al. |
| 2014/0076246 A1 | 3/2014 | Komatsubara et al. |

FOREIGN PATENT DOCUMENTS

| | | | | |
|---|---|---|---|---|
| JP | 8-71103 A | | 3/1996 | |
| JP | 2001-346827 A | | 12/2001 | |
| JP | 2003047360 A | * | 2/2003 | ............ A01K 23/00 |
| JP | 2003-245024 A | | 9/2003 | |
| JP | 2004-194566 A | | 7/2004 | |
| JP | 2004-195254 A | | 7/2004 | |
| JP | 2006-271212 A | | 10/2006 | |
| JP | 2007-167007 A | | 7/2007 | |
| JP | 2012-205542 A | | 10/2012 | |

* cited by examiner

Front →

ABSORBENT ARTICLE FOR PET ANIMALS

RELATED APPLICATIONS

The present application is a National Phase of International Application Number PCT/JP2014/065950, filed Jun. 16, 2014, which claims priority to Japanese Application Number 2014-118171, filed Jun. 6, 2014.

TECHNICAL FIELD

The present invention relates to absorbent articles used to absorb body exudates of pet animals (often designated simply as pet) such as dogs and cats.

BACKGROUND

Conventionally, absorbent articles for pet animal used to be put on the body of pet animal such as dog or cat is known. For example, Patent Literature 1 discloses an absorbent article for pet animal having a longitudinal direction and a transverse direction and including an absorbent panel having a ventral region, a dorsal region, an intermediate region extending between the dorsal region and the ventral region, a liquid-permeable internal sheet, a liquid-impermeable external sheet and an absorbent core interposed between the interior and exterior sheets, and connector tape means to connect the ventral region with the dorsal region. In addition, elastic elements are arranged on the outer sides in the longitudinal direction of front and rear end edges of the absorbent core so that these elastic elements may be stretch and contract at least in the transverse direction.

CITATION LIST

Patent Literature

{PTL 1}: JP 2007-167007 A

SUMMARY

Technical Problem

For the absorbent article for pet animal disclosed in Patent Literature 1, the absorbent core is not influenced by contraction of the elastic elements when the dorsal region is coupled with the ventral region by the tape means since the elastic elements are distanced from the both end edges of the absorbent core by a predetermined dimension in the longitudinal direction. This suggests an anxiety that the absorbent core might be displaced and fit thereof to the body of pet animal may be disturbed, for example, due to the movements of the pet animal wearing the article. Especially, the end edges of the absorbent core located in the ventral region are apt to be separated from the body of pet animal due to movement of the body of pet animal and apt to cause leakage of body exudates as the case may be.

An object of the present invention is to improve the conventional absorbent articles for pet animal and to provide an absorbent article for pet animal ensuring a high fit of the absorbent core along the end edges thereof to the body of pet animal.

Solution to Problem

The present invention relates to an improvement in an absorbent article for pet animal having a longitudinal direction and a transverse direction being orthogonal thereto and including an absorbent panel having a body-contact surface facing a body of pet animal, a non-body-contact surface opposite thereto, a ventral region, a dorsal region and an intermediate region extending between the ventral region and the dorsal region wherein the absorbent panel includes a liquid-permeable interior sheet, a liquid-impermeable exterior sheet and an absorbent core interposed between these interior and exterior sheets.

The absorbent article for pet animal according to the present invention lies in that, further including a ventral side elastic element extending in the transverse direction in the ventral region; the absorbent core is located in an area extending from an opening provided in the intermediate region for insertion of pet animal's tail toward the side of the ventral region and the absorbent core has a first end portion located on the side of the ventral region; and the first end portion of the absorbent core overlaps the ventral side elastic element in a planar view.

Advantageous Effects of Invention

In the absorbent article for pet animal according to one or more embodiments of the present invention, the ventral side elastic element overlaps the first end portion of the absorbent core in a planar view and, for this reason, with the article put on the body of pet animal, the first end portion of the absorbent core is kept in contact with the body of pet animal at a sufficiently high degree of fit to restrict leakage of body exudates due to separation of the first end portion from the body of pet animal.

BRIEF DESCRIPTION OF DRAWINGS

The drawings illustrate specific embodiments of the present invention including optional and preferred embodiments as well as essential features of the invention.

FIG. 3 (a) is a schematic sectional view taken along line IIIa-IIIa in FIG. 2 and FIG. 3 (b) is a schematic sectional view taken along line IIIb-IIIb in FIG. 7.

FIG. 8 (a) is a diagram illustrating a handling to put the absorbent article on the body of pet animal and FIG. 8 (b) is a diagram illustrating a state of an absorbent core when the absorbent article has been partially inserted into a space defined between both rear legs of pet animal in the course of putting the article on the body of pet animal.

DESCRIPTION OF EMBODIMENTS

The embodiments described below relate to an absorbent article as illustrated in FIGS. 1-11, including both optional and preferred features as well as those features which are essential features of the present invention.

First Embodiment

Referring to FIGS. 1 through 4, an absorbent article 10 for pet animal (often designated simply as "pet") has a longitudinal direction Y and a transverse direction X and includes the absorbent panel 14 having a body-contact surface facing the body of pet animal, a non-body-contact surface lying on a side opposite to the body-contact surface, a ventral region 11, a dorsal region 12 and an intermediate region 13 extending in the longitudinal direction Y between the ventral region 11 and the dorsal region 12, and a pair of fastening tabs 15 outward extending in the transverse direction X from both side edges of the ventral region 11 to define a fastening system. The ventral region 11 and the dorsal region 12 are respectively adapted to cover an abdominal area and a lumbar area both located anterior to rear legs 7 of a pet animal 5 and the intermediate region 13 means the region adapted to cover buttocks inclusive of an area defined between thighs of the rear legs 7. The absorbent article 10 has a longitudinal axis P bisecting a dimension thereof in the transverse direction X and a transverse axis Q bisecting a dimension thereof in the longitudinal direction Y.

The fastening tab 15 is provided on the non-body-contact surface with a first fastening element 18 having hooks of a mechanical fastener. The dorsal region 12 is provided on the exterior surface thereof with a landing area 20 extending in the transverse direction X and having a second fastening element 19 having loops of the mechanical fastener so that the first fastening element 18 on the fastening tab 15 may be releasably caught by the second fastening element 19 on the landing area 20. The landing area 20 is attached on the exterior surface of the dorsal region 12, for example, with hot melt adhesives (not shown).
<Absorbent Panel>

The absorbent panel 14 is contoured by first and second end edges 14a 14b opposed to each other in the longitudinal direction Y and both side edges (peripheries of leg-openings) concavely extending in the longitudinal direction Y between the first and second end edges 14a, 14b. The absorbent panel 14 further includes a liquid-permeable interior sheet 22 formed of, for example, fibrous nonwoven fabrics, porous plastic films or laminated sheets thereof and lying on the side of the body-contact surface, a liquid-impermeable exterior sheet 23 lying on the exterior surface of the absorbent panel 14 and lying on the exterior surface, i.e., on the non-body contact surface of the absorbent panel 14 and formed of moisture-permeable plastic films, fibrous nonwoven fabrics or laminated sheets thereof, and a liquid-absorbent layer 25 interleaved between these interior and exterior sheets 22, 23. The interior sheet 22 and the exterior sheet 23 extend outward beyond a peripheral edge of the liquid-absorbent layer 25 and are bonded to each other by the intermediary of, for example, hot melt adhesive (not shown) distributed to an interior surface of at least one of the both sheets 22, 23 in the area extending outward beyond the peripheral edge of the liquid-absorbent layer 25.

Between the interior sheet 22 and the exterior sheet 23, a leakage-barrier sheet 26 formed of liquid-impermeable but moisture-permeable plastic films is allocated on the side of the non-body-contact surface of the liquid-absorbent layer 25 and secured with, for example, hot melt adhesives (not shown) distributed to any one of the both sheets 22, 23. In addition, outside of the transverse direction X of the liquid-absorbent layer 25 lying on the body-contact surface of the interior sheet 22, a pair of containment sheets 28 arranged symmetrically about the longitudinal axis P.

The absorbent panel 14 is defined by first and second end portions 31, 32 opposed to each other in the longitudinal direction Y and extending in the transverse direction X and both lateral portions 34 opposed to each other in the transverse direction X and extending in the longitudinal direction Y. With the absorbent article 10 put on the body of pet animal, the respective first fastening elements 18 on a pair of the fastening tabs 15 are caught by the second fastening element 19 allocated on the exterior surface of the dorsal region 12 so as to form a waist-opening and a pair of leg-openings (See FIG. 1).

Figure 1:
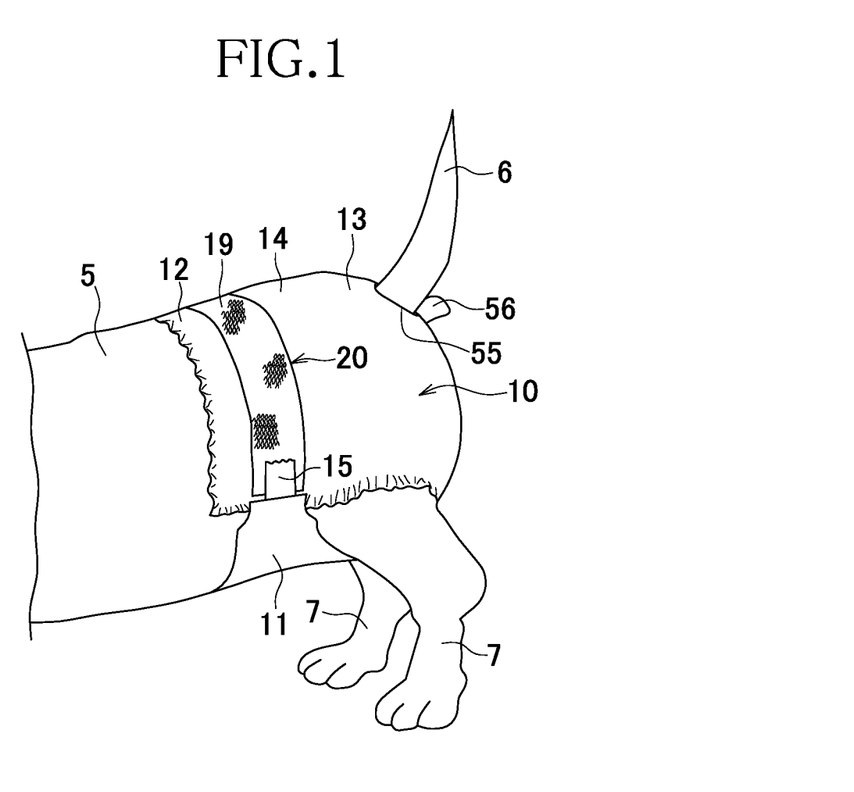
FIG. 1 is a perspective view illustrating an absorbent article for pet animal according to a first embodiment in the configuration it would assume when placed on a dog as an example of the absorbent article according to the present invention.
Figure 2:
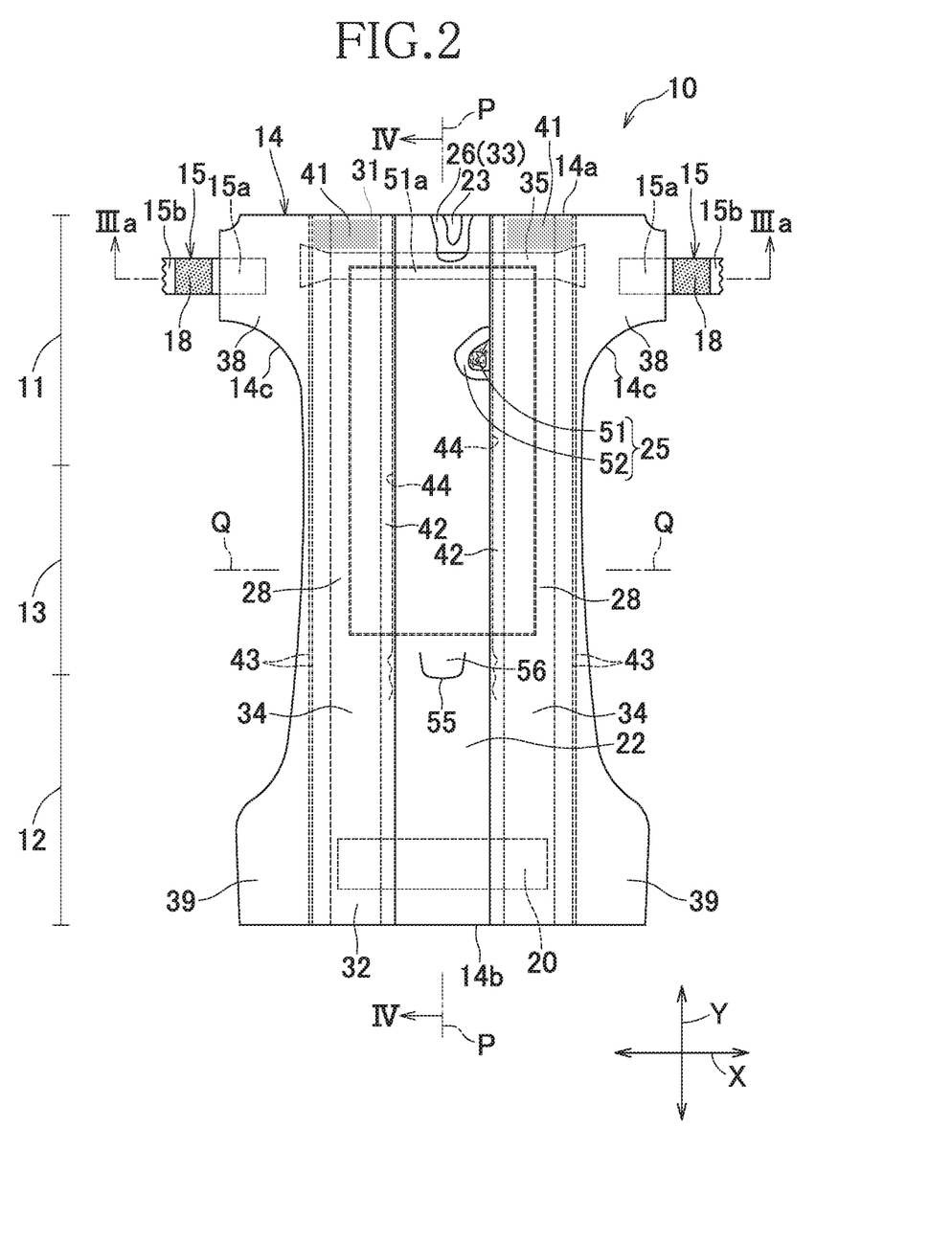
FIG. 2 is a partially cutaway plan view of the absorbent article flatly developed until respective elastic elements have been stretched in a longitudinal direction as well as in a transverse direction to the respective maximum elongations (until gathers due to contractions of the respective elastic elements substantially disappear).
Figure 3:
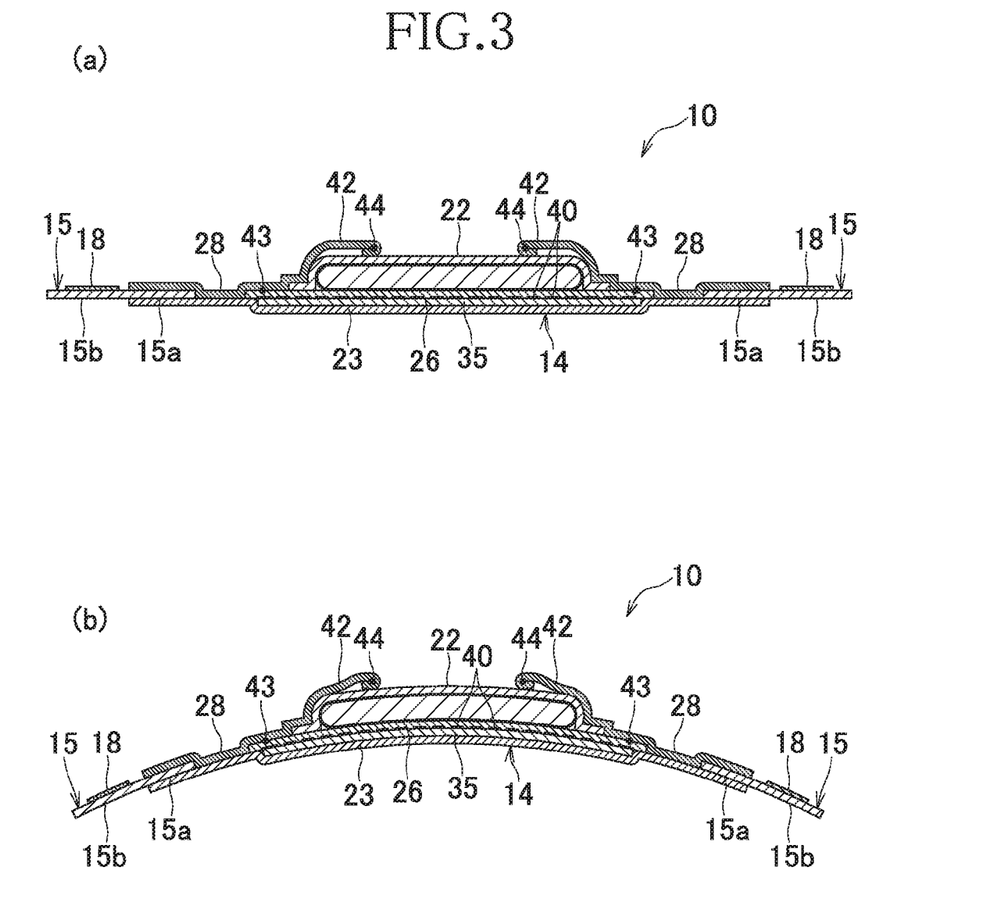
Figure 4:
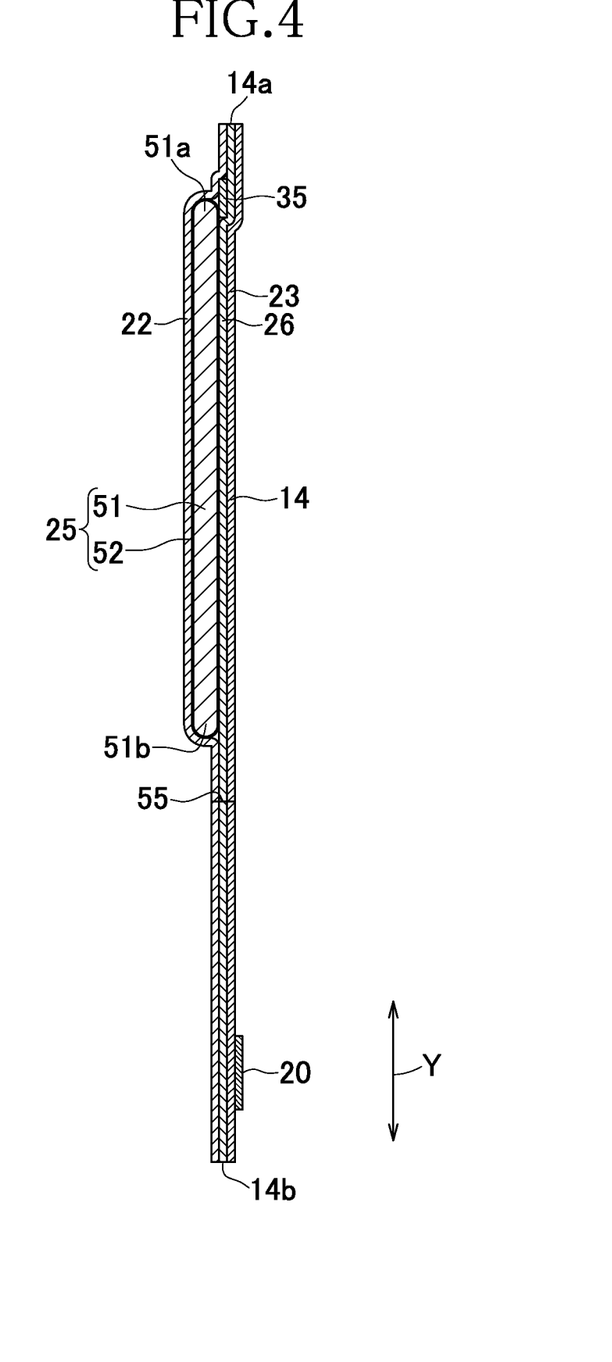
FIG. 4 is a schematic sectional view taken along line IV-IV in FIG. 2.

Referring to FIG. 2 and FIG. 3 (a), a first end portion 31 of the absorbent panel 14 is provided with a ventral side ribbon-like elastic element (ventral side elastic element) 35 interleaved between the exterior sheet 23 and the leakage-barrier sheet 26 so as to extend in the transverse direction X. The ventral side ribbon-like elastic element 35 may be a string-, flat-rubber (urethane foam)- or ribbon-like elastic element formed of natural or synthetic rubber or polyurethane form and, in the present embodiment, the elastic element formed of polyurethane form is provided. The ventral side ribbon-like elastic element 35 preferably has a width dimension (dimension in the longitudinal direction Y) ensuring a relatively wide area of the ventral region 11 to be kept in close contact with the body of pet animal at a high degree of fit under a contractile force of the ventral side ribbon-like elastic element 35. Specifically, referring to FIG. 6, a length dimension (dimension in the transverse direction X) L1 of the ventral side ribbon-like elastic element 35 is in a range of about 180 to about 220 mm and a width dimension (dimension in the longitudinal direction Y) W1 of the ventral side ribbon-like elastic element 35 in a central portion is in a range of about 20 to about 40 mm.

Referring to FIG. 3 (b) and FIG. 6, the ventral side ribbon-like elastic element 35 and a first end portion 51a of an absorbent core 51 described later overlap each other in a planar view so that the portion of the absorbent core 51 on the side of the non-body-contact surface may contract relative to the portion of the absorbent core 51 on the side of the body-contact surface under contraction of the ventral side ribbon-like elastic element 35 and, in consequence, the first end portion 51a of the absorbent core 51 is convexly curved. According to the present embodiment, the ventral side ribbon-like elastic element 35 is attached to the leakage-barrier sheet 26 by the intermediary of discontinuously arranged joints 40, for example, formed of hot melt adhesives distributed thereto so as to be spaced apart from each other in the transverse direction X. Compared with where a single joint 40 continuously extends in the transverse direction X, portions of the absorbent core 51 on the side of the non-body-contact surface defined between each pair of the adjacent joints 40 more effectively contract to make the convex curve appearing in the first end portion 51a of the absorbent core 51 more distinctive.

Referring to FIG. 2, in the ventral region 11 and the dorsal region 12, the exterior sheet 23 and the containment sheets 28 extend outward in the transverse direction X beyond the respective lateral portions of the interior sheet 22 and the leakage-barrier sheet 26 defining the both lateral portions 34 of the absorbent panel and overlap each other to form ventral side flaps 38 and dorsal side flaps 39. Respective proximal portions 15a of a pair of fastening tabs 15 are integrally interposed between areas of the exterior sheet 23 and the containment sheets 28 defining together the respective ventral side flaps 38 and secured therebetween, for example, with hot melt adhesives (not shown) distributed to respective interior surfaces of the both sheets 23, 28.

In the fastening system composed of the first fastening elements 18 and the second fastening element 19, it is possible to replace hooks in the first fastening elements 18 by pressure-sensitive adhesive as long as desired peel strength is assured. Here, surfaces of the respective first fastening elements 18 are preferably covered with silicon-coated separators. Respective base material sheets for the fastening tabs 15 are preferably made from sheet materials having relatively a high stiffness and a tensile strength, for example, plastic films, fibrous nonwoven fabrics, laminates thereof or craft paper. As long as the desired advantageous effects of the present invention are ensured, it is also possible to attach the first fastening elements 18 to the ventral side flaps 38 without the use of the fastening tabs 15 so that the first fastening elements 18 may be directly releasably caught by the second fastening element 19.

The containment sheet 28 has the proximal portion partially defining the lateral portion 34, front and rear portions (fixed portions) 41 fixed to the body-contact surface of the interior sheet 22 and the exterior sheet 23 in the ventral and dorsal regions 11, 12 and a distal portion 42 formed by folding back inward the inner side edge portion of the containment sheet 28 and extending in the longitudinal direction Y between the front and rear fixed end portions. Outside the side edge of the leakage-barrier sheet 26 as viewed in the transverse direction X, a plurality of, for example, three strand- or string-like lateral-elastic elements 43 extending in the longitudinal direction Y are contractibly secured between the proximal portion of the containment sheet 28 and the side edge of the exterior sheet 23 with hot melt adhesives (not shown). A plurality of, for example, two strand- or string-like containment-elastic elements 44 extending in the longitudinal direction Y are contractibly secured under tension to the distal portion 42. With the absorbent article put on the body of pet animal, the respective distal portions 42 are distanced from the body-contact surface of the interior sheet 22 under contraction of the containment-elastic elements 44 to form a pair of leakage-barriers serving to prevent body exudates from leaking out.

Referring to FIG. 2, the front end portion 41 on the side of the ventral region 11 of the containment sheet 28 is located outward of the first end portion 51a of the absorbent core 51 as viewed in the longitudinal direction Y. The front end portion 41 is located between the end edge of the first end portion 51a of the absorbent core 51 and the first end edge 14a of the absorbent panel 14 and, for this reason, there is no possibility that an elasticity of the front end portion 41 might be affected by rigidity of the absorbent core 51. In consequence, there is no anxiety that a standing behavior of the leakage-barrier cuffs might be limited, causing leakage of body exudates. In addition, it is assured to restrict a possibility that, in the course of handling to put the article on the body of pet animal as described later, the first end portion 31 and the second end portion 32 of the absorbent panel 14 formed of sheet materials only might be stretched until the absorbent article become shapeless. In this way, the developed figuration of the absorbent article 10 is stably maintained.

In the present embodiment, the lateral-elastic elements 43 and the containment-elastic elements 44 are formed of, for example, string- or strand-like elastic materials having a fineness in a range of about 280 to about 500 dtex and contractibly secured under tension at a stretch ratio in a range of about 2.0 to about 3.0, preferably in a range of about 2.2 to about 2.5. A distance dimension (i.e., pitch) in a plurality of the elastic elements 43, 44 may be appropriately set depending on the contractile force required for the respective elastic elements 43, 44. It is also possible to set the fineness as well as the stretch ratio of the elastic material used for the respective elastic elements 43, 44 so as to be not uniform but to be different from each other. Specifically, it is possible, for example, to set the fineness of elastic materials for the lateral-elastic elements 43 in such a manner that the outermost elastic material as viewed in the transverse direction X has the fineness larger than that of innermost elastic materials as viewed in the transverse direction X or, in reverse, the former is smaller than the latter. Furthermore, it is also possible to set the fineness or the stretch ratio of the respective elastic materials so as to increase (or decrease) gradually from the inner side toward the outer side as viewed in the transverse direction X.

In the present embodiment, the lateral-elastic elements 43 fully extend across the absorbent panel 14 in the longitudinal direction Y, i.e., continuously extend in the longitudinal direction Y from the first end edge 14a to the second end edge 14b. The containment-elastic elements 44 extend from the first end edge 14a across the liquid-absorbent layer 25 into the dorsal region 12. The lateral-elastic elements 43 and the containment-elastic elements 44 have elastically functioning portions which practically develop an elasticity and elastically non-functioning portions which snapped back in the course of securing these elastic elements to the respective sheets ("snap back" means a phenomenon such that the portions of the elastic elements not secured to the associated sheets move back under their own contraction to the vicinities of the ends of respective secured portions). The respective ends of the lateral-elastic elements 43 and the containment-elastic elements 44 are located to overlap the both end portions of the ventral side ribbon-like elastic element 35 in planar view and these end portions preferably define the elastically functioning portions which practically develop the elasticity. As long as such condition is met, the first end portion 31 of the absorbent panel 14 will be pulled toward the side of the dorsal region 12 under the contractile force of the both elastic elements 43, 44 and the both lateral portions 34 as a whole will be under tension so that the developed figuration of the absorbent article 10 may be maintained. In this way, as will be described later, it is possible to carry the handling of the absorbent article 10 to put on the body of pet animal smoothly without an anxiety that the absorbent article 10 might become shapeless when a part of the absorbent article 10 is passed between the rear legs 7 of pet animal.

<Liquid-Absorbent Layer>

The liquid-absorbent layer 25 is located in an area partially defined by the ventral region 11 and the intermediate region 13 and includes the semirigid absorbent core 51 formed of a mixture of superabsorbent polymer (SAP) particles having a water-absorption capacity at least 10 times as high as own weight thereof, wood fluff pulp and optionally a small amount of thermoplastic fibers and a core wrapping sheet 52 formed of hydrophilic and liquid-diffusible nonwoven fabrics or tissue paper adapted to cover the core 51. The core wrapping sheet 52 is bonded to the interior sheet 22 and/or the leakage-barrier sheet 26, for example, with hot melt adhesives and extends outward in the transverse direction X beyond the side edges of the absorbent core 51 in the ventral region 11.

Figure 5:
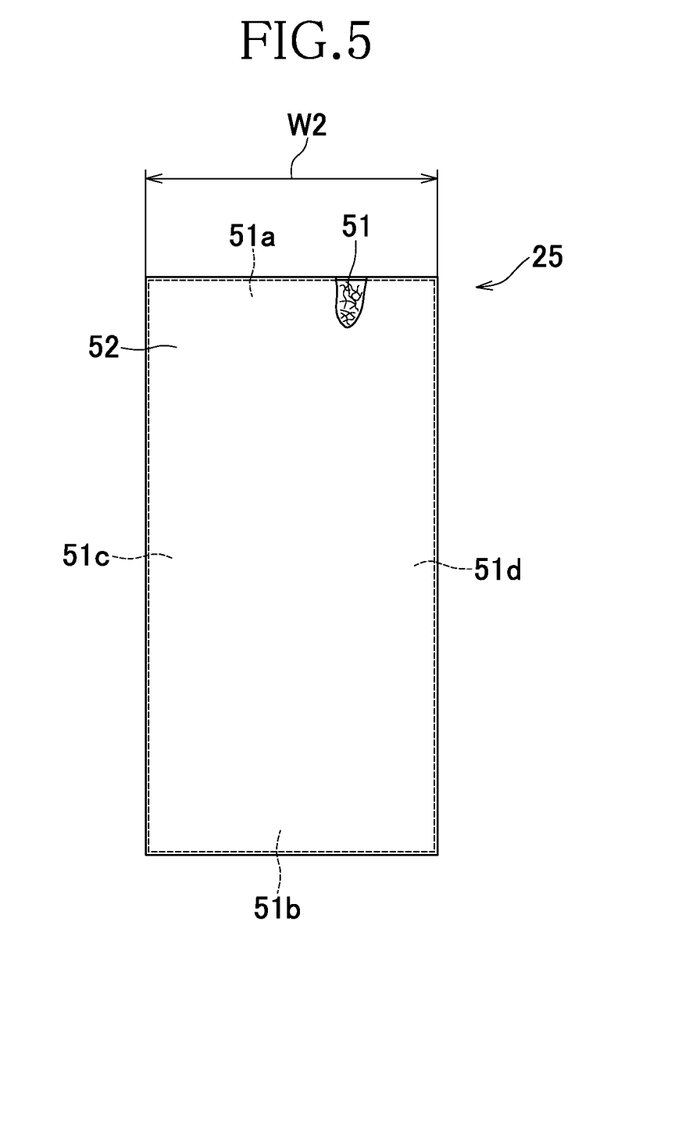
FIG. 5 is a partially cutaway plan view of a liquid-absorbent layer.

Referring to FIG. 5, the absorbent core 51 has a longitudinally long rectangular shape contoured by first and second 51a, 51b distanced from and opposed to each other in the longitudinal direction Y and rectilinearly extending in the transverse direction X and both side edge portions 51c, 51d extending in the longitudinal direction Y between the first and second end portions 51a, 51b. As has been previously described, the first end portion 51a of the absorbent core 51 and the ventral side ribbon-like elastic element 35 overlap each other in a planar view. While the core wrapping sheet 52 and the absorbent core 51 are substantially the same in shape as well as in size in the present embodiment, it is possible to arrange so that the core wrapping sheet 52 and the absorbent core 51 may be different from each other in the shapes and part of the core wrapping sheet 52 may extend outward beyond a peripheral edge of the absorbent core 51 to form flaps as long as the advantageous effects of the present invention as described later are ensured. Furthermore, the shape of the absorbent core 51 is not limited to the shape as illustrated in the present embodiment but may have the various well known shapes, for example, the front and rear end edges may be curved as a whole or the side edges may be rectilinear or curved as a whole.

In the present embodiment, the liquid-absorbent layer 25 is located in the ventral region 11 and the intermediate region 13 and not in the dorsal region 12. Regardless whether the bet animal is male or female, a position of urinal organs of pet animal is biased forward with respect to the tail 6 and there is no possibility that any amount of urine might move rearward as long as pet animal is in a usual standing posture. For this reason, it is essential to locate the liquid-absorbent layer 25 at least the intermediate region 13 and the ventral region 11 both facing the urinal organs of pet animal. By adopting such particular location of the liquid-absorbent layer 25, it is possible to improve an absorbent efficiency of the liquid-absorbent layer 25 and to reduce a manufacturing cost composed with where the liquid-absorbent layer 25 is arranged so as to extend to the dorsal region 12 not directly influenced by urination.

At a position of the absorbent article slightly deviated from the liquid-absorbent layer 25 toward the dorsal region 12, a slit 55 for formation of an opening (insertion opening) into which the tail 6 of pet animal is inserted. The slit 55 is approximately in U-shape and extends through the interior sheet 22, the leakage-barrier sheet 26 and the exterior sheet 23 overlapping each other in a planar view. The absorbent panel 14 may be partially cut and a tongue-shaped portion 56 including the respective sheets 22, 23, 26 bonded or non-bonded to each other may be folded outward to form the opening. Preferably, the opening has an appropriate size not only suitable for insertion of the tail 6 but also for facing an anus so that the body exudates (feces) discharged from the anus may be further discharged outward. By inserting the tail 6 into the opening and exposing the anus, it is possible to prevent the body exudates received by the absorbent panel 14 from adhering to fur of pet animal. The tongue-shaped portion 56 may be removed (cut away) from the absorbent panel 14 to prevent the body exudates discharged from the anus from adhering to the tongue-shaped portion 56.

Figure 6:
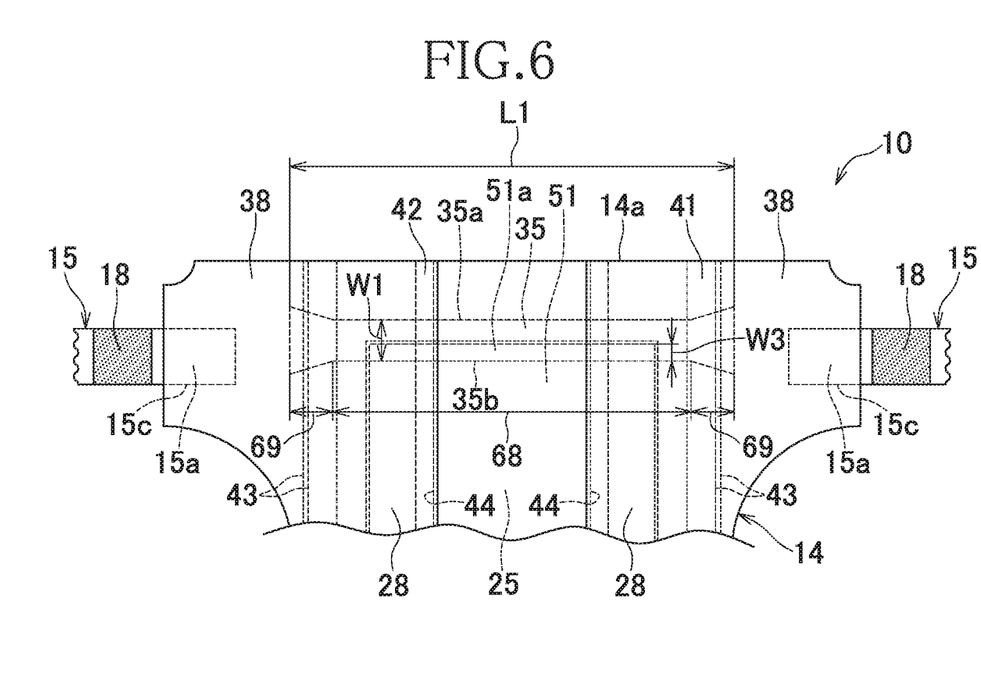
FIG. 6 is a scale-enlarged plan view of a ventral region of the absorbent article flatly developed in the same manner as FIG. 2.
Figure 7:
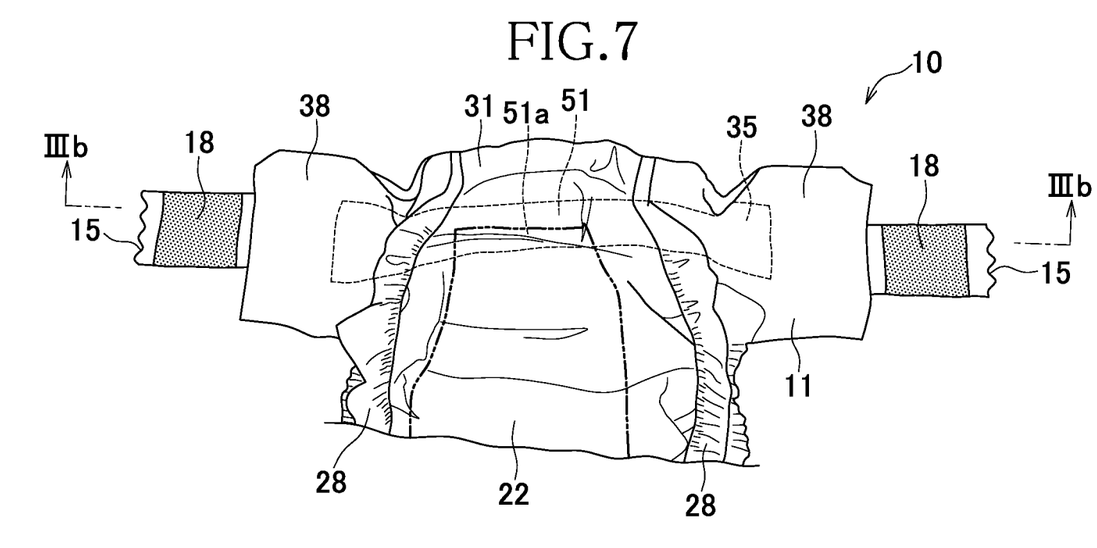
FIG. 7 is a scale-enlarged plan view of the ventral region as viewed from an interior side of the absorbent article in the natural state (in which respective elastic elements are in a state of contraction).

Referring to FIGS. 5 through 7, the ventral side ribbon-like elastic element 35 has an outer end edge 35a, an inner end edge 35b, a mid portion 68 and both side edge portions 69 lying on both sides of in the transverse direction X of the mid portion 68 each having a width larger (in the longitudinal direction Y) than that of the mid portion 68. In the mid portion 68, the ventral side ribbon-like elastic element 35 overlaps the first end portion 51a of the absorbent core 51. The both end portions of the semirigid absorbent core 51 usually have rigidity higher than that of the other constituent materials formed of, for example, fibrous nonwoven fabrics and there is an anxiety that these end portions might be displaced from contact with the body of pet animal due to the movement of the body of pet animal, causing leakage of the body exudates. However, with the arrangement according to the present embodiment such that the ventral side ribbon-like elastic element 35 contractibly secured under tension between the absorbent core 51 and the exterior sheet 23 overlaps the first end portion 51a of the absorbent core 51 in planar view, the first end portion 51a of the absorbent core 51 is kept in close contact with the body of pet animal under the extensional stress of the ventral side elastic element 35 at high fit. In this regard, it is possible to provide the ventral side ribbon-like elastic element 35 having a shape different from that in the present embodiment, for example, a rectangular ventral side ribbon-like elastic element having a uniform width dimension fully over from the mid portion 68 to the both side edge portions 69.

To ensure a desired fit of the absorbent core 51 to the body of pet animal, a width dimension W2 of a mid portion in the first end portion 51a of the absorbent core 51 is preferably at least in a range of 80 to 150.0 mm or more. In the case of the width dimension W2 of 80 mm or less, it will be impossible to prevent floating off of the first end portion 51a from the body of pet animal even when the first end portion 51a overlaps the ventral side elastic element 35 in a planar view. For the absorbent article not of pull-on type but of open type, the fastening tabs 15 and the ventral side ribbon-like elastic element 35 are preferably arranged so as to be approximately aligned with each other in the transverse direction X. Specifically, when an end edge of the first end portion 51a of the absorbent core 51 lies on the outer side in the longitudinal direction Y of an inner end edge (corresponding to an end edge on the side of the dorsal region 12) 15c of at least one of the pair of fastening tabs 15, the first end portion 51a of the absorbent core 51 is put in close contact with the body of pet animal at a higher fit when the pair of fastening tabs 15 are pulled in opposite directions in the course of putting the absorbent article on the body of pet animal.

Figure 8:
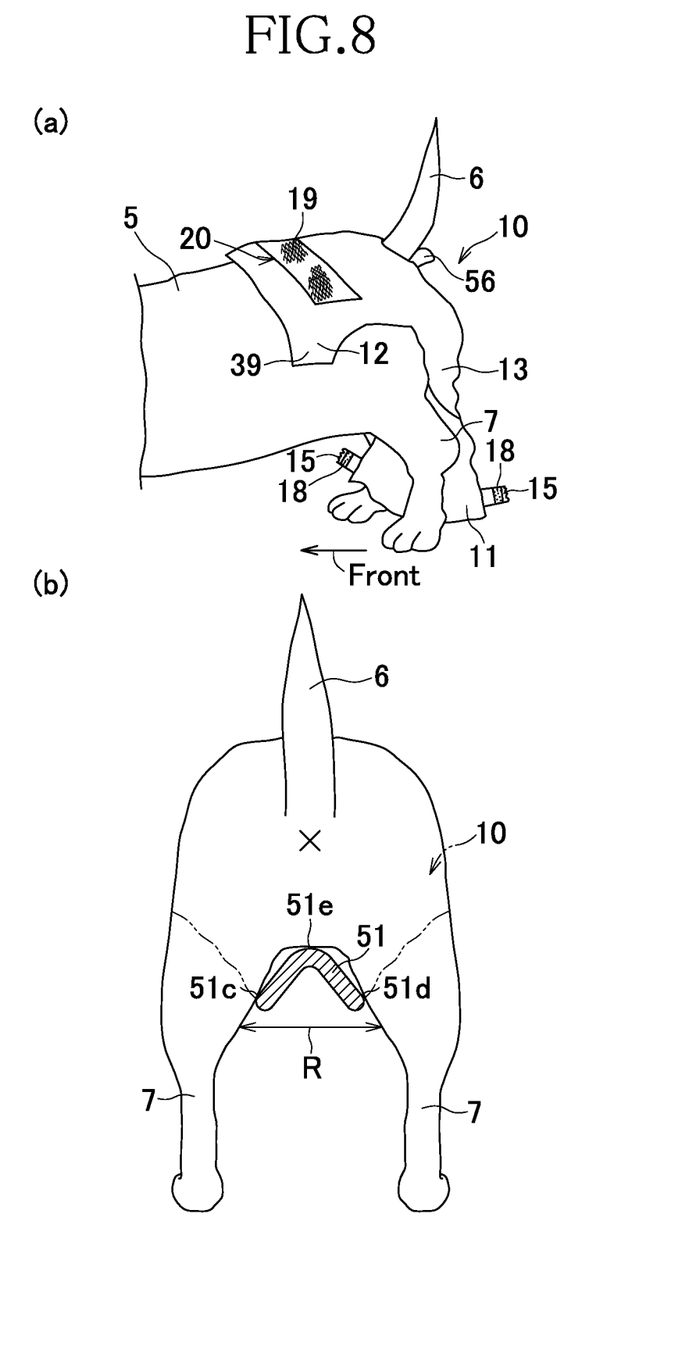
Figure 9:
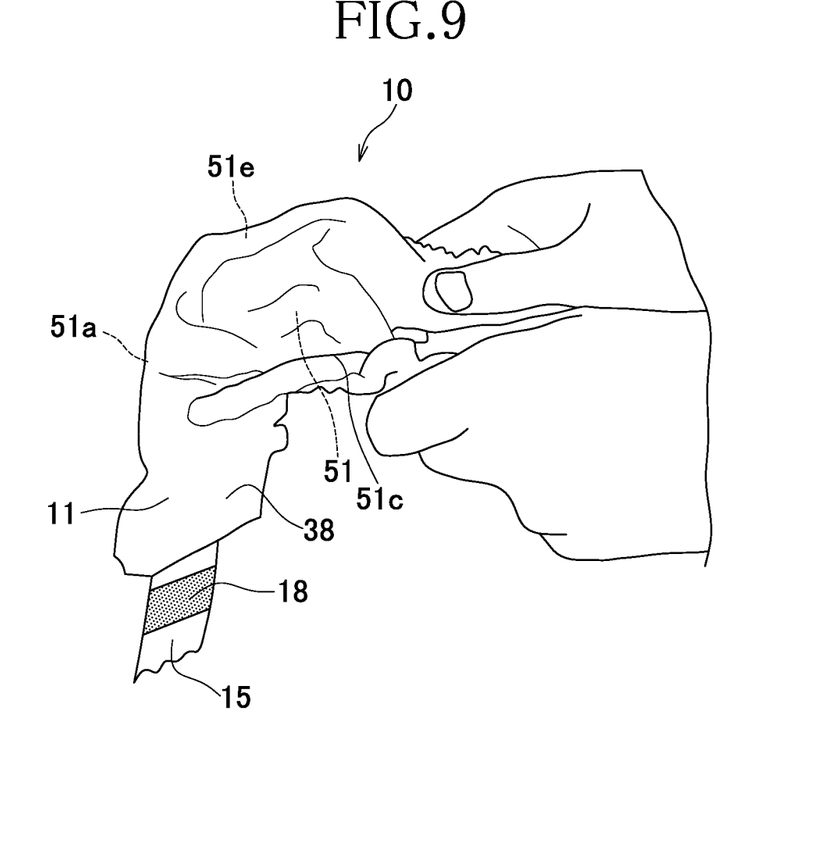
FIG. 9 is a diagram illustrating a state in which an handling person grips the absorbent article in the course of putting the absorbent article on the body of pet animal.

Referring to FIG. 8 (a) and FIG. 9, when the absorbent article 10 is put on the body of pet animal 5 in standing posture, a handler may partially cut the intermediate region 13 along the slit 55 to form the opening, insert the tail 6 of pet animal 5 into this opening and the dorsal region 12 may be appropriately located on a back of pet animal 5. Then the handler may grip the ventral region 11 hanging down along the back of pet animal 5, pull the ventral region 11 to a position facing the dorsal region 12, now pinch lugs 15b of the respective fastening tabs 15 and overlap these tabs 15 on the landing area 20 so that first fastening elements 18 may be caught by the second fastening element 19. Such sequences may be followed to put the absorbent article 10 on the body of pet animal 5 in the standing posture without placing pet animal in supine or side lying posture. In the course of such method to put the absorbent article 10 on the body of pet animal, when the ventral region 11 is passed between the rear legs 7 and pulled forward, the ventral side flaps 38 formed of fibrous nonwoven fabrics hang down and the both side edge portions 51c, 51d of the absorbent core 51 are indirectly put to the interior sides of the respective rear legs 7. For this reason, if the absorbent core 51 is relatively wide, i.e., the dimension W2 in the transverse direction X thereof is larger than the dimension R between the rear legs 7, the first end portion 51a will be partially caught by the rear legs 7 and folded, making it impossible to put the absorbent article on the body of pet animal smoothly. However, if the width dimension W2 of the absorbent core 51 is set to a relatively small dimension and to make the absorbent core 51 narrower as a whole, it will be no more possible to assure the desired absorption capacity thereof since the area of the absorbent core 51 as a whole will be unacceptably reduced.

The both side edge portions 51c, 51d of the absorbent core 51 are indirectly put to the interior sides of the respective rear legs 7 in the course of inserting the first end portion 31 of the absorbent core 14 between the rear legs 7 and, for this reason, it is possible for the handler to insert the first end portion 31 stably without being required for the handler to grip the ventral region 11. However, if the absorbent core 51 is dimensioned to be relatively narrow, the both side edge portions 51c, 51d will not be applied to the interior sides of the respective rear legs 7 and no more function as guides for smooth advancement of the ventral region 11.

As previously described, the width dimension W2 of the first end portion 51a of the absorbent core 51 is narrowed under the contractile force of the ventral side ribbon-like elastic element 35 and, in view of this, even if the width dimension W2 is slightly larger than the distance dimension R between the rear legs 7, it is possible to restrict the anxiety that the both side edge portions 51c, 51d of the absorbent core 51 may be caught by the rear legs 7. In addition, the first end portion 51a of the absorbent core 51 has its bending rigidity enhanced composed with the other portions and, in consequence, there is no possibility that the first end portion 51a might be deformed even under a force functioning to fold the first end portion 51a in the course of passing between the rear legs 7.

In the natural state of the absorbent article 10, the ventral side ribbon-like elastic element 35 is in contracted state and the lateral-elastic elements 43 or the containment-elastic elements 44 extending across the ventral side ribbon-like elastic element 35 are also in a contracted state. Thus, not only the first end portion 51a, the absorbent core 51 as a whole is a 3D configuration convexly curved toward the body of pet animal 5. Referring to FIG. 8 (b), such convexly curved 3D configuration of the absorbent core 51 makes it possible for the side edge portions 51c, 51d of the absorbent core 51 to be put to the interior sides of the respective rear legs 7 in the course of putting the article on the body of pet animal and for the mid portion 51e to be put to the crotch region of pet animal. In this way, it is possible to restrict the possibility that the absorbent article 10 might be folded or twisted composed with where the both side edge portions 51c, 51d are exclusively put to the body of pet animal.

It is possible for the absorbent core 51 to be convexly curved toward the body of pet animal 5 under contraction of the respective elastic elements 35, 43, 44, and it is also possible for the absorbent core 51 to be convexly curved in the reverse direction as the absorbent core 51 as a whole is pushed in the direction in which the absorbent core 51 is distanced from the body of pet animal. In the latter, the absorbent core 51 is concavely curved relative to the body of pet animal and, particularly when the article is put on a male dog, it is possible to restrict the anxiety that the urinary organs might be caught by part of the absorbent article 10. While it may be appropriately selected depending on factors such as the sex whether the absorbent core 51 should be convexly curved toward the body of pet animal as in the present embodiment or concavely curved relative to the body of pet animal, it is more facilitated to pinch the pinch lugs 15b of the respective fastening tabs 15 when the absorbent core 51 is convexly curved toward the body of pet animal as in the present embodiment since the ventral side flaps 38 hang down from the absorbent core 51 under own mass of these side flaps 38.

As has been described hereinbefore, the ventral side ribbon-like elastic element 35 and the first end portion 51a of the absorbent core 51 overlap each other in a planar view and, for this reason, with the article 10 put on the body of pet animal, the dimension in the transverse direction X of the first end portion 51a is relatively small and the bending stiffness thereof is relatively high. In this way, it is possible to pass the ventral region 11 smoothly between the rear legs 7 from the rear side of the pet animal 5. Further, with the article 10 put on the body of pet animal, the ventral side ribbon-like elastic element 35 is stretched in a circumferential direction around the waist to assure that the first end portion 51a is put in close contact in its expanded state with the body of pet animal at a high degree of fit. In this regard, while the absorbent article 10 according to the present embodiment may be used for every kind of pet animal having four limbs whether the pet animal is male or female, the article 10 according to the present embodiment may be favorably used for female dog and female cat in view of the fact that the urinary organ is positioned so as to face the ventral region 11 and there is no anxiety that the urinary organ might be tightened by the ventral side ribbon-like elastic element 35 and create a feeling of discomfort.

Second Embodiment

Figure 10:
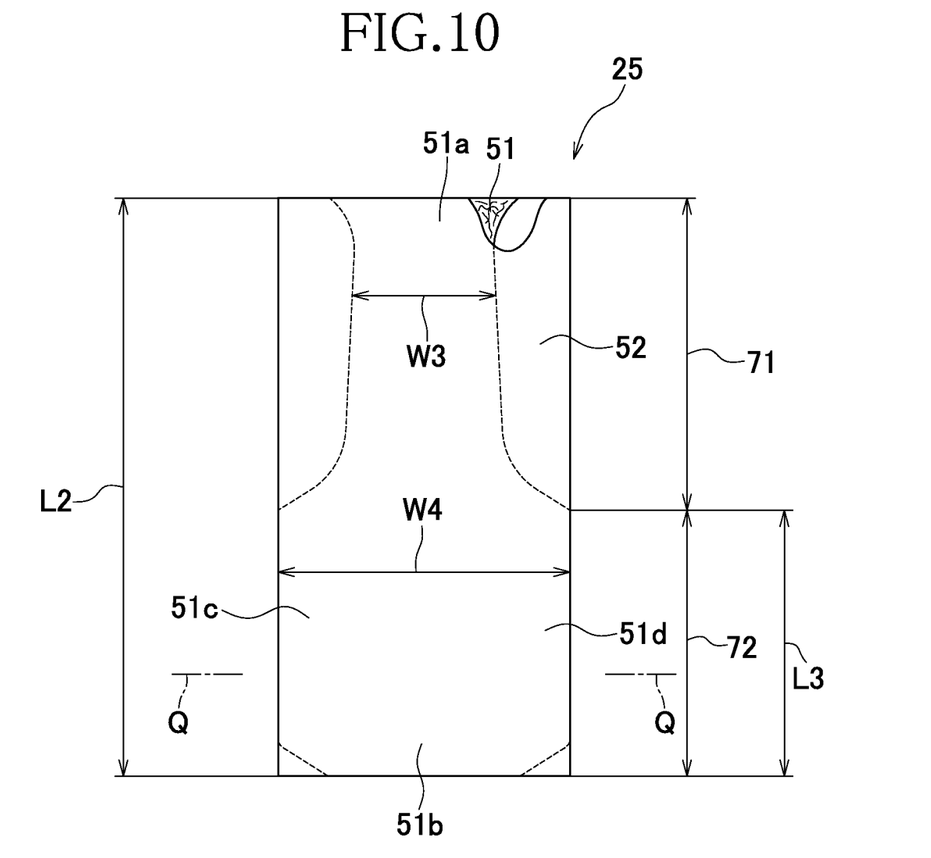
FIG. 10 is a partially cutaway plan view similar to FIG. 5, illustrating the liquid-absorbent layer according to a second embodiment.

Referring to FIG. 10, a basic arrangement of the absorbent article 10 according to the present embodiment is the same as the basic arrangement of the first embodiment and only aspects distinguished from these in the first embodiment will be described hereunder.

The absorbent core 51 according to the present embodiment has first and second portions 51a, 51b distanced from each other in the longitudinal direction Y and extending in the transverse direction X and both side edge portions 51c, 51d extending in the longitudinal direction Y between the first and second end portions 51a, 51b and, for the convenience of illustration, divided into a small width region 71 which is located on the side of the first end portion 51a and relatively narrow and a large width region 72 which is located on the side of intermediate region 13 so as to extend across the transverse axis Q and relatively wide. Both side edges of the width small region 71 are concavely curved and both side edges of the width large region 72 are rectilinear. An end edge of the second end portion 51b has a rectilinear portion located so as to be opposite to an end edge of the first end portion 51a and gradient portions defined at both sides in the transverse direction X of the rectilinear portion and obliquely extending from the rectilinear portion. A dimension in the transverse direction X of the first end portion 51a is substantially the same to a dimension in the transverse direction X of the rectilinear portion in the end edge of the second end portion 51b. The small width region 71 is gradually narrowed from the side of the intermediate region 13 to the side of the ventral region 11.

The width large region 72 is located on the side of the intermediate region 13 facing the urinary organ makes it possible to absorb urine even when a large amount of urine has been discharged and the width small region 71 located on the side of the ventral region 11 not facing the urinary organ makes it possible to absorb and retain the urine diffused in the absorbent core 51 at a high efficiency. In particular, in the case of male pet animal, for example, male dog, an orifice of the urinary organ points forward and the liquid-absorbent layer 25 located on the side of the ventral region 11 makes it possible to absorb urine reliably.

The small width region 71 of the absorbent core 51 located anteriorward makes it possible to prevent a movement forward of the rear legs 7 during walking from being embarrassed by rigidity of the absorbent core 51. In order that urine can be reliably absorbed and retained on the side of the intermediate region 13 and diffused urine can be reliably retained on the side of the ventral region 11, a dimension L3 in the longitudinal direction Y of the large width region 72 is preferably in a range of about 30 to about 70% of a dimension L2 in the longitudinal direction Y of the absorbent core 51 as a whole and a dimension (width dimension) W3 in the transverse direction X of the narrowest portion in the small width region 71 is preferably in a range of about 30 to about 70% of a dimension (width dimension) W4 in the transverse direction X of the widest portion in the large width range 72.

Figure 11:
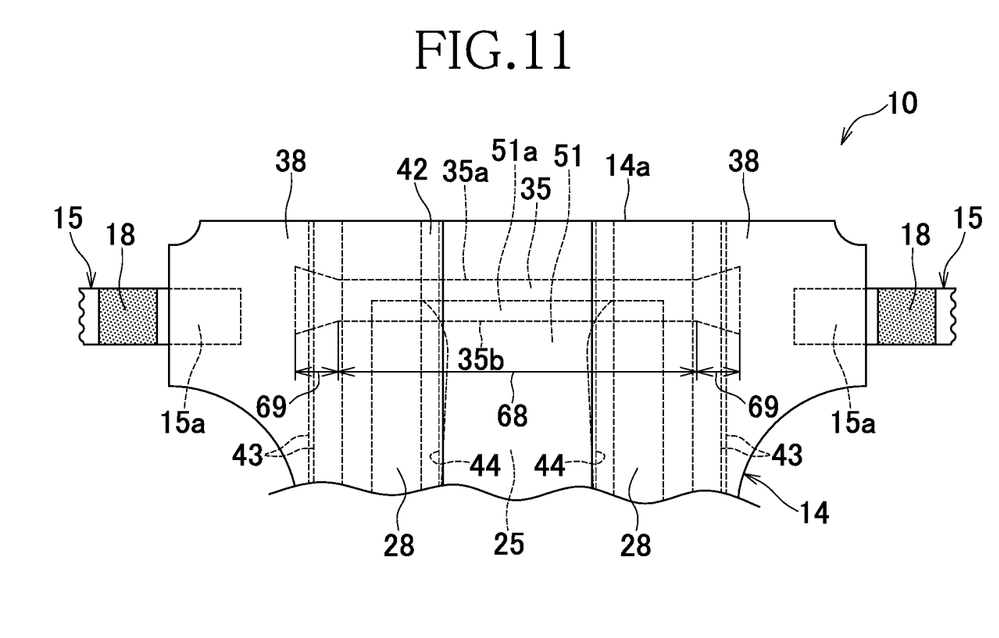
FIG. 11 is a scale-enlarged plan view similar to FIG. 6, illustrating the ventral region in the absorbent article according to the second embodiment.

Referring to FIG. 11, the first end portion 51a of the absorbent core 51 (small width range 71) is located so as to overlap the ventral side ribbon-like elastic element 35 in planar view and, in consequence, the first end portion 51a is contracted under the contraction of the ventral side ribbon-like elastic element 35 so that the absorbent core 51 may be easily inserted between the rear legs 7 of pet animal 5. Furthermore, the small width region 71 has a shape gradually tapered toward the ventral region 11 and, consequently, it is possible to insert the absorbent core 51 smoothly even when the distance dimension R between the rear legs 7 is relatively small. Compared with where the width dimension of the absorbent core is drastically varied in stepwise fashion, it is possible to pass the absorbent core between the rear legs 7 without an anxiety that the core might be indirectly caught by the rear legs 7.

The constituent elements of the absorbent article 10 are not limited to those described in the present specification but the other various types of material widely used in the relevant technical field may be used without limitation unless otherwise stated. Terms such as "first" and "second" used in the specification and claims of the present specification are used merely to distinguish the similar elements, similar positions or the other similar means.

The disclosure relating to the present invention as described hereinbefore may be arranged at least as follows.

An absorbent article for pet animal having a longitudinal direction and a transverse direction being orthogonal thereto and including an absorbent panel having a body-contact surface facing a body of pet animal, a non-body-contact surface opposite thereto, a ventral region, a dorsal region and an intermediate region extending between the ventral region and the dorsal region wherein the absorbent panel includes a liquid-permeable interior sheet, a liquid-imper meable exterior sheet and an absorbent core interposed between these interior and exterior sheets, wherein:

the article further includes ventral side elastic element extending in the transverse direction in the ventral region; the absorbent core being located in an area extending from an opening provided in the intermediate region for insertion of pet animal's tail toward the side of the ventral region and the absorbent core having a first end portion located on the side of the ventral region; and the first end portion of the absorbent core overlaps the ventral side elastic element in a planar view.

The present invention disclosed in the above paragraph may include embodiments at least as described hereinafter. The embodiments may be adopted separately or in combination.

(1) The ventral side elastic element is contractibly secured under tension between the absorbent core and the external sheet so that the first end portion of the absorbent core may be convexly curved from the side of the non-body-contact surface toward the side of the body-contact surface under contraction of the ventral side elastic element.

(2) The ventral side elastic element is formed of ribbon-like elastic material extending in the transverse direction.

(3) An absorbent article further including a pair of fastening tabs extending outward from both side edges of the ventral region wherein an end edge of the first end portion is located on the outer side in the longitudinal direction of an end edge of at least one of the pair of fastening tabs lying on the side of the dorsal region.

(4) An absorbent article further including a pair of containment sheets attached to the body-contact surface of the interior sheet wherein each of the containment sheets has a proximal portion fixed to the interior sheet and a distal portion adapted to be distanced from the interior sheet under contraction of the containment-elastic element extending in the longitudinal direction and wherein the fixed portion of the distal portion on the side of the ventral region is out of overlapping relation with the absorbent core in planar view.

(5) An absorbent article further including a lateral-elastic elements' attached between the interior sheet and the respective proximal portions wherein the absorbent core is convexly curved toward the side of the body-contact surface or the non-body-contact surface under contraction of the ventral side elastic element and contraction of at least one of the containment-elastic element and the lateral elastic element.

(6) A portion of which the contractile force actually functions in at least one of the containment-elastic element and the lateral elastic element overlaps the ventral side elastic element in planar view.

(7) The absorbent core further includes a second end portion lying on the side of the dorsal region and a dimension in the transverse direction of the first end portion is smaller than a dimension in the transverse direction of the second end portion.

(8) The absorbent core is divided into a small width region having the first end portion and a large width region having the second end portion and, in the small width region, a width dimension of the absorbent core gradually decreases from the side of the intermediate region toward the side of the ventral region.

The invention claimed is:

1. An absorbent article for a pet animal, said absorbent article comprising:
   a longitudinal direction and a transverse direction being orthogonal to the longitudinal direction,
   an absorbent panel having a body-contact surface for facing a body of the pet animal, a non-body-contact surface opposite to the body-contact surface, a ventral region, a dorsal region and an intermediate region extending between the ventral region and the dorsal region wherein the absorbent panel includes a liquid-permeable interior sheet, a liquid-impermeable exterior sheet and an absorbent core interleaved between the interior and exterior sheets, and a ventral side elastic element extending in the transverse direction in the ventral region, wherein the absorbent core is located in an area extending from an opening provided in the intermediate region for insertion of a tail of the pet animal toward of the ventral region, the absorbent core has a first end portion located toward the ventral region, the first end portion of the absorbent core overlaps the ventral side elastic element in a planar view, and the ventral side elastic element is contractibly secured under tension between the absorbent core and the exterior sheet so that the first end portion of the absorbent core is convexly curved in a direction from the non-body-contact surface toward the body-contact surface under contraction of the ventral side elastic element.

2. The absorbent article according to claim 1, wherein the ventral side elastic element is formed of ribbon elastic material extending in the transverse direction.

3. The absorbent article according to claim 1, further comprising a pair of fastening tabs extending outward from two side edges of the ventral region, wherein an end edge of the first end portion of the absorbent core is located on an outer side in the longitudinal direction with respect to an end edge of at least one of the pair of fastening tabs.

4. The absorbent article according to claim 1, further comprising a pair of containment sheets attached to the body-contact surface of the interior sheet, wherein each of the containment sheets has
a containment-elastic element extending in the longitudinal direction;
a proximal portion having a fixed portion fixed to the interior sheet; and
a distal portion adapted to be distanced from the interior sheet under contraction of the containment-elastic element, and wherein the fixed portion of the proximal portion on the side of the ventral region does not overlap the absorbent core in the planar view.

5. The absorbent article according to claim 4, further comprising lateral-elastic elements secured between the interior sheet and the corresponding proximal portions, wherein the absorbent core is convexly curved toward the body-contact surface under contraction of the ventral side elastic element and contraction of at least one of the containment-elastic elements and the lateral-elastic elements.

6. The absorbent article according to claim 5, wherein at least one of the containment-elastic elements and the lateral elastic elements overlaps the ventral side elastic element in the planar view.

7. The absorbent article according to claim 1, wherein the absorbent core further includes a second end portion lying toward the dorsal region, and a dimension of the first end portion in the transverse direction is smaller than a dimension of the second end portion in the transverse direction.

8. The absorbent article according to claim 7, wherein the absorbent core is divided into a small width region having the first end portion and a large width region having the second end portion, and in the small width region, a width dimension of the absorbent core gradually decreases from the intermediate region toward the side of the ventral region.

\* \* \* \* \*